United States Patent [19]
Yang et al.

[11] Patent Number: 5,824,030
[45] Date of Patent: Oct. 20, 1998

[54] LEAD WITH INTER-ELECTRODE SPACING ADJUSTMENT

[75] Inventors: Weiqun Yang, San Jose; Peter A. Altman, San Francisco, both of Calif.

[73] Assignee: Pacesetter, Inc., Sunnyvale, Calif.

[21] Appl. No.: 576,873

[22] Filed: Dec. 21, 1995

[51] Int. Cl.⁶ ................................................. A61N 1/05
[52] U.S. Cl. ........................................ 607/122; 600/374
[58] Field of Search .................................. 607/116, 119, 607/122; 600/374

[56] References Cited

U.S. PATENT DOCUMENTS

| | | | |
|---|---|---|---|
| 3,974,834 | 8/1976 | Kane | 128/419 |
| 4,603,705 | 8/1986 | Speicher et al. | 128/786 |
| 4,721,118 | 1/1988 | Harris | 128/785 |
| 4,735,205 | 4/1988 | Chachques et al. | 128/419 |
| 4,744,370 | 5/1988 | Harris | 128/786 |
| 4,913,164 | 4/1990 | Greene et al. | 128/785 |
| 5,127,403 | 7/1992 | Brownlee | 128/419 |
| 5,489,275 | 2/1996 | Thompson et al. | 604/264 |

*Primary Examiner*—William E. Kamm
*Assistant Examiner*—Kennedy J. Schaetzle
*Attorney, Agent, or Firm*—Steven M. Mitchell

[57] ABSTRACT

A single-pass transvenous lead for atrial sensing and pacing, ventricular sensing and pacing, as well as for ventricular and atrial defibrillation. The lead optimizes the positioning of the electrodes in various patients regardless of variations in these patients' hearts, by enabling independent adjustment of the spacing between various pacing, sensing and defibrillation electrodes, before and after implantation or insertion in the heart. The lead includes an elongated lead body, an outer sheath that extends coaxially with the lead body, and two atrial windows positioned along the outer sheath, adjustable relative to a reference point such as a distal pacing tip. The outer sheath includes an atrial section that is slidably adjustable along the lead body by means of an expandable member.

22 Claims, 15 Drawing Sheets

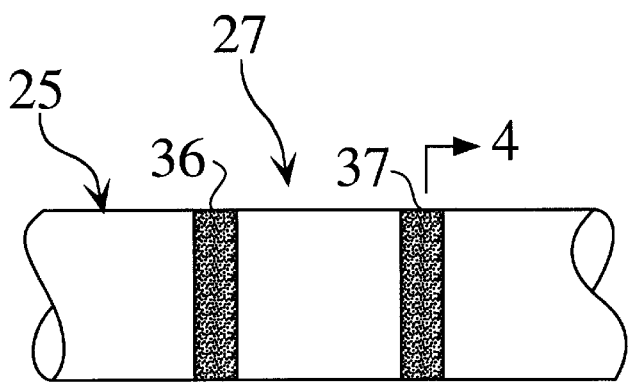
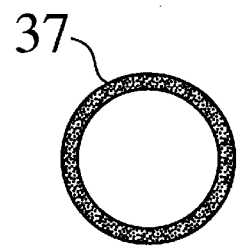
Fig. 3　　　　Fig. 4
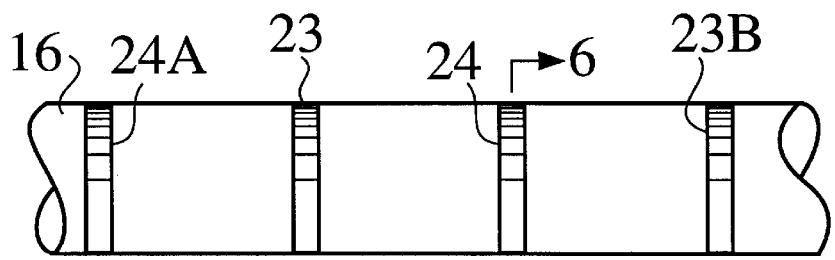
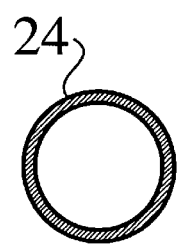
Fig. 5　　　　Fig. 6
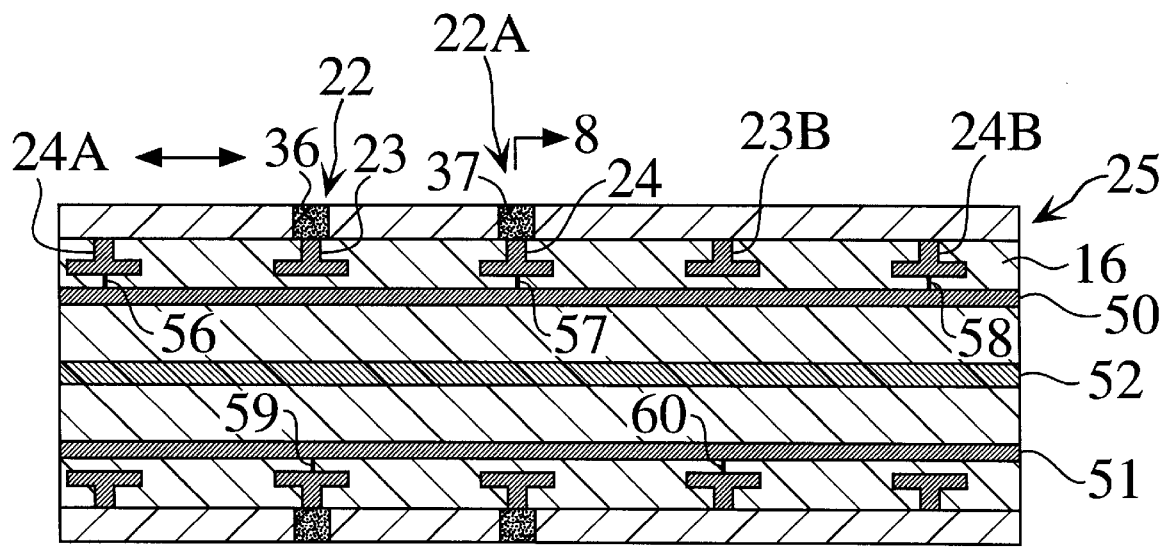
Fig. 7

LEAD WITH INTER-ELECTRODE SPACING ADJUSTMENT

BACKGROUND OF THE INVENTION

1. Field of the Invention

The present invention relates in general to the field of implantable medical devices, and it particularly relates to a lead or catheter with a mechanism for adjusting inter-electrode spacing. The invention more specifically relates to a single-pass transvenous lead for atrial sensing and pacing, ventricular sensing and pacing, as well as ventricular and atrial defibrillation. Among other features, this new design facilitates the implantation procedure of antiarrhythmic devices, and optimizes the positioning of electrodes.

2. Background Art

Various types of transvenous pacing and cardioversion/defibrillation leads have been developed for endocardial introduction into different chambers of a patient's heart, typically the right ventricle or right atrium, as well as the coronary sinus. These flexible leads are usually constructed with an outer insulator sheath, such as a flexible silicone or polyurethane tube or coating for encasing one or more electrical coiled wire conductors. One such conductor is typically attached at its distal tip to the shank portion of a tip electrode. In bipolar or multipolar leads one or more coiled wire conductors are provided in a coaxial or collinear relation to a first coiled wire conductor, and are connected to ring-shaped electrodes situated along the lead body. The proximal ends of the conductors are coupled to a connector which includes a single pin in unipolar leads and additional pins or rings in bipolar and multipolar leads.

The tip electrode is usually placed in contact with the myocardial tissue by passage through a venous access, often the subclavian or cephalic vein or one of its tributaries, which leads to the endocardial surface of the heart chambers. The tip electrode may be held in place passively by means of tines within the trabeculations of myocardial tissue, or actively through the use of an actively manipulated anchor or screw that penetrates the myocardium, as described, for example, in U.S. Pat. No. 3,974,834.

The distal ends of many available leads include silicone or polyurethane flexible tines or fins which extend outward and are usually molded separately and bonded onto the distal end of the lead, usually proximal to the tip electrode. These passive fixation mechanisms allow surrounding growth of encapsulating tissue in chronically implanted leads to secure the electrode tip in position against the heart wall, and to prevent dislodgment of the tip during the life of the lead, thus maintaining consistent sensing and pacing characteristics over time.

In some instances, it may be desirable to add one or more leads to stimulate different portions of the heart than are presently being stimulated with leads already in place. There is a considerable number of patients who have had one or more, and sometimes as many as four or five previously and currently used leads in their veins and heart. The risks of removing leads or introducing additional leads in the heart and venous path include the following: an increased likelihood of infection; physiological complications; obstruction to blood flow; or an increased likelihood of the formation of blood clots which may embolize to the lung and produce severe complications and even death. In addition, extra leads in the heart can interfere with cardiac valve and mechanical function, and can cause considerable difficulty in the positioning and attachment of endocardial leads in the heart.

In multiple lead systems, leads are passed parallel to each other through the accessible veins. The situation can result in the dislodgment of a first lead which has been initially inserted into a proper position in the heart. Further, when multiple leads are inserted in different portions of the heart, the leads sometimes rub against each other due to lead flexing caused by the beating of the heart, resulting in damage to the insulative coating. The forces produced as a result of the rubbing sometimes cause dislodgment of electrodes attached to the leads. Additionally, the use of multiple conductors, may disadvantageously increase the lead diameter, and may prevent the introduction of new leads.

Therefore, it is desirable to minimize the number of implanted leads, since a fewer number of leads reduces the probability of occurrence of the foregoing exemplary risks. It is also desirable to facilitate the placement of these leads and to optimize the positioning of the electrodes.

In recent years there has been a great deal of interest and progress in the integration of implantable medical devices such as defibrillators and pacemakers. For the purpose of this application, "defibrillation" is used in a broad sense, as including the application of relatively high energy and high voltage shocks to the heart to terminate tachyarrhythmias including fibrillation and pathologic tachycardias. Similarly, "pacing" is used in a broad sense, as including the application of relatively low energy and low voltage pacing pulses to maintain an adequate heart rate or to break a tachyarrhythmia by stimulating the patient's heart.

The present trend to integrate the various leads of several medical devices may result in an increase in the number of leads. As an example, one such integral lead may include six or more different spacings between the various electrodes, such as the relative spacings between the RV defibrillation electrode, the atrial sense/pace electrode, and the SVC defibrillation electrode, leading to nine different spacing combinations for each patient. Such leads will render the selection process more confusing for the surgeons, and will increase the development and storage costs.

Illustrations of lead integration can be found in U.S. Pat. No. 4,603,705 to Speicher et al., and U.S. Pat. No. 5,127,403 to Brownlee. A limitation of these conventional leads resides in their lack of flexibility to readily accommodate various patients with different heart and chest sizes, due to the non adjustable inter-electrode spacing.

In order to address this concern, lead manufacturers produce several leads, each with different inter-electrode spacing. Prior to implanting these leads, the surgeon makes a calculated guess based on the patient's body size. If after implantation the surgeon discovers that the selected lead was not optimally selected, he/she implants a new lead and discards the old lead. This will increase the surgery cost and will delay the surgical procedure.

Guessman et al., in A New Method for Choosing the Proper Atrial Lead Setback Spacing for Single Pass VDD Leads, NASPE Abstracts, PACE, Vol. 18, Part II, No. 457, April 1995, briefly describes a method for minimizing the waste of permanent leads relative to the standard chest X-ray method. However, this method does not seem to have universal applicability beyond VDD lead sizing.

Therefore, there is still a significant and still unsatisfied need for a multiple conductor endocardial lead or catheter assembly, that can be used almost universally in conjunction with electrodes with various functions, including but not limited to ventricular pacing and sensing, atrial sensing and pacing, as well as with other vascular electrodes. This lead or catheter assembly permits independent adjustment of the spacing between the various electrodes, before and after implantation or insertion in the heart or along the venous path.

SUMMARY OF THE INVENTION

The present invention provides a lead or catheter with a mechanism for adjusting inter-electrode spacing.

More particularly, the invention provides a single-pass transvenous lead for atrial sensing and pacing, ventricular sensing and pacing, as well as for ventricular and atrial defibrillation, which optimizes the positioning of electrodes in various patients regardless of variations in these patients' hearts.

The present invention also provides a multiple-conductor endocardial lead which allows independent adjustment of the spacing between the various pacing, sensing and defibrillation electrodes, before and after implantation or insertion in the heart or along the venous path.

In addition, the new lead design minimizes the number of conductors connecting the various electrode elements. It simplifies the lead selection process for the various patients, and it further reduces the implantation time and the amount of hardware residing in the patient's venous and cardiac systems.

Briefly, the foregoing and other objects and features of the present invention are realized by providing a new lead which includes an elongated lead body, an outer sheath that extends coaxially with the lead body, and two atrial windows positioned along the outer sheath. These atrial windows are adjustable relative to a reference point such as a distal pacing tip. The outer sheath includes an atrial section that is slidably adjustable along the lead body by means of an expandable member.

In one embodiment the lead body includes a plurality of adjacent electrode elements, and the outer sheath includes a pair of windows that are slidably positionable over, and in registration with a pair of electrode elements, in order to electrically expose the electrode elements to define a pair of effective atrial electrodes. These windows are preferably made of biocompatible, porous material in the slidable sheath. However, the windows could be simply cutouts in the sheath.

In another embodiment, the outer sheath includes a pair of diagonally opposing windows that are shaped and positioned on the outer sheath so as to overlay a selected pair of the plurality of atrial electrode elements in order to electrically expose the selected pair of atrial electrode elements.

In yet another embodiment, the lead includes a right ventricular defibrillation (RV) electrode positioned along the distal end of the lead body, and a superior vena cava (SVC) defibrillation electrode comprised of an SVC electrode formed on the lead body, and a window which forms part of the outer sheath and which slidably covers and electrically exposes at least part of the SVC electrode, so as to define an effective SVC defibrillation electrode therewith.

In still another embodiment, the lead includes a distal assembly, an intermediate assembly and a proximal assembly, that are movable relative to one another by using internal lead bodies connected to the two most distal assemblies and the electrodes therein.

BRIEF DESCRIPTION OF THE DRAWINGS

The above and other features of the present invention and the manner of attaining them, will become apparent, and the invention itself will be best understood, by reference to the following description and the accompanying drawings, wherein:

FIGS. 3 and 4 are enlarged side elevational and sectional views, respectively, of part of an outer sheath used in the lead of FIG. 1;

FIGS. 5 and 6 are enlarged side elevational and sectional views, respectively, of part of an atrial section forming part of a lead body of the lead of FIG. 1;

FIGS. 7 and 8 are greatly enlarged cross sectional views of part of the atrial section of the lead of FIG. 1, showing the outer sheath of FIG. 3 assembled over the lead body, with a pair of windows in contact and in registration with a pair of atrial electrode elements;

Similar numerals refer to similar elements in the drawing. It should be understood that the sizes of the different components in the figures may not be in exact proportion, and are shown for visual clarity and for the purpose of explanation.

DETAILED DESCRIPTION OF THE PREFERRED EMBODIMENT

Figure 1:
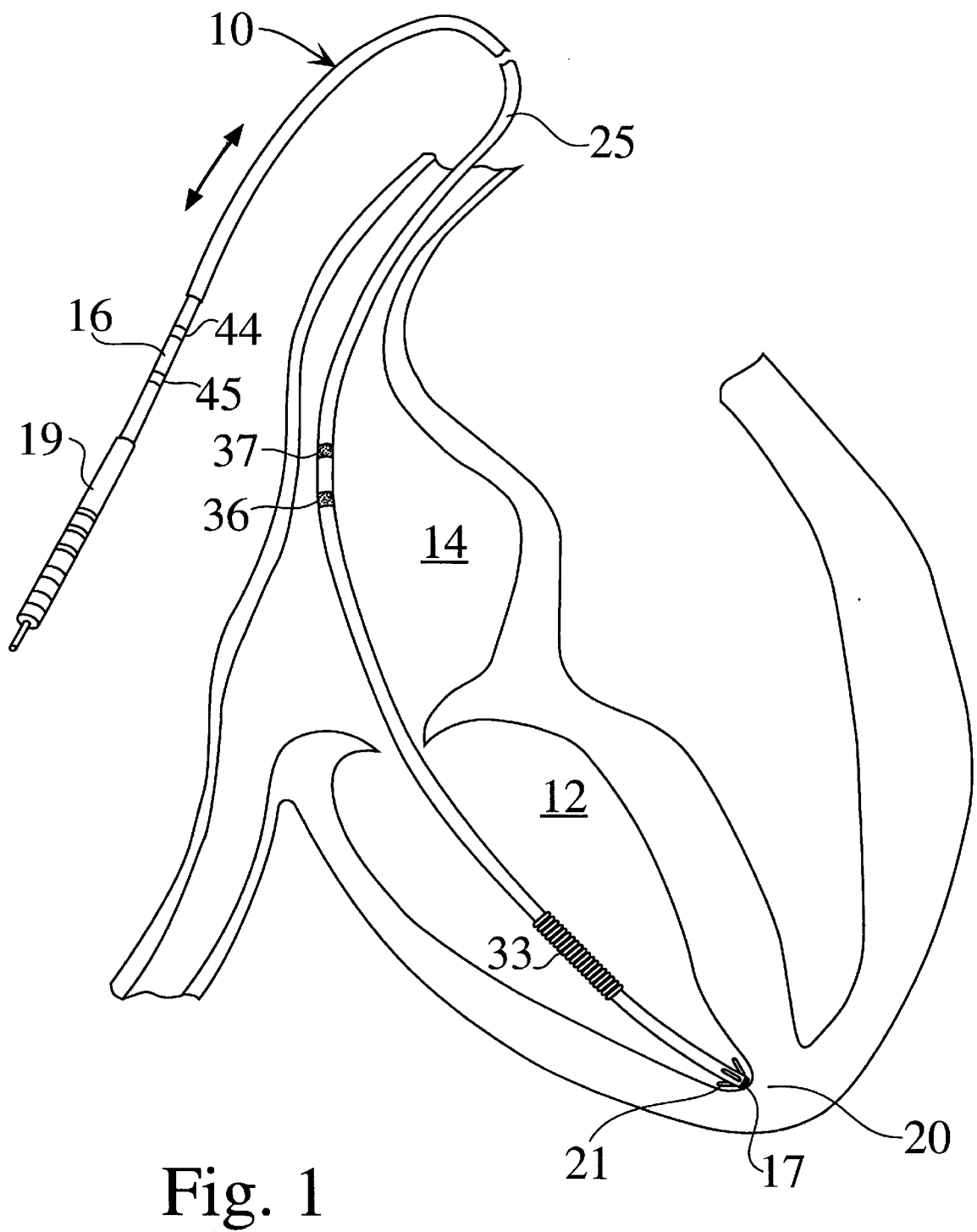
FIG. 1 is a schematic view of a transvenous pacing lead according to the present invention, shown introduced in the right ventricle for ventricular sensing and pacing, and through the right atrium for atrial sensing and pacing.

FIG. 1 shows a transvenous pacing lead 10 introduced in the right ventricle 12 for ventricular sensing and/or pacing, and through the right atrium 14 for atrial sensing and/or pacing. The lead 10 generally includes a lead body 16 that extends between a distal or pacing tip 17 at its distal end, and a connector 19 at its proximal end for connection to a pacemaker (not shown). The pacing tip 17 is positioned against the apex 20 of the right ventricle 12 by means of a plurality of tines 21, and in time becomes securely attached to the ventricle wall by endothelial or fibrotic tissue forming around the distal end of the lead, and particularly around the tines 21.

Figure 2:
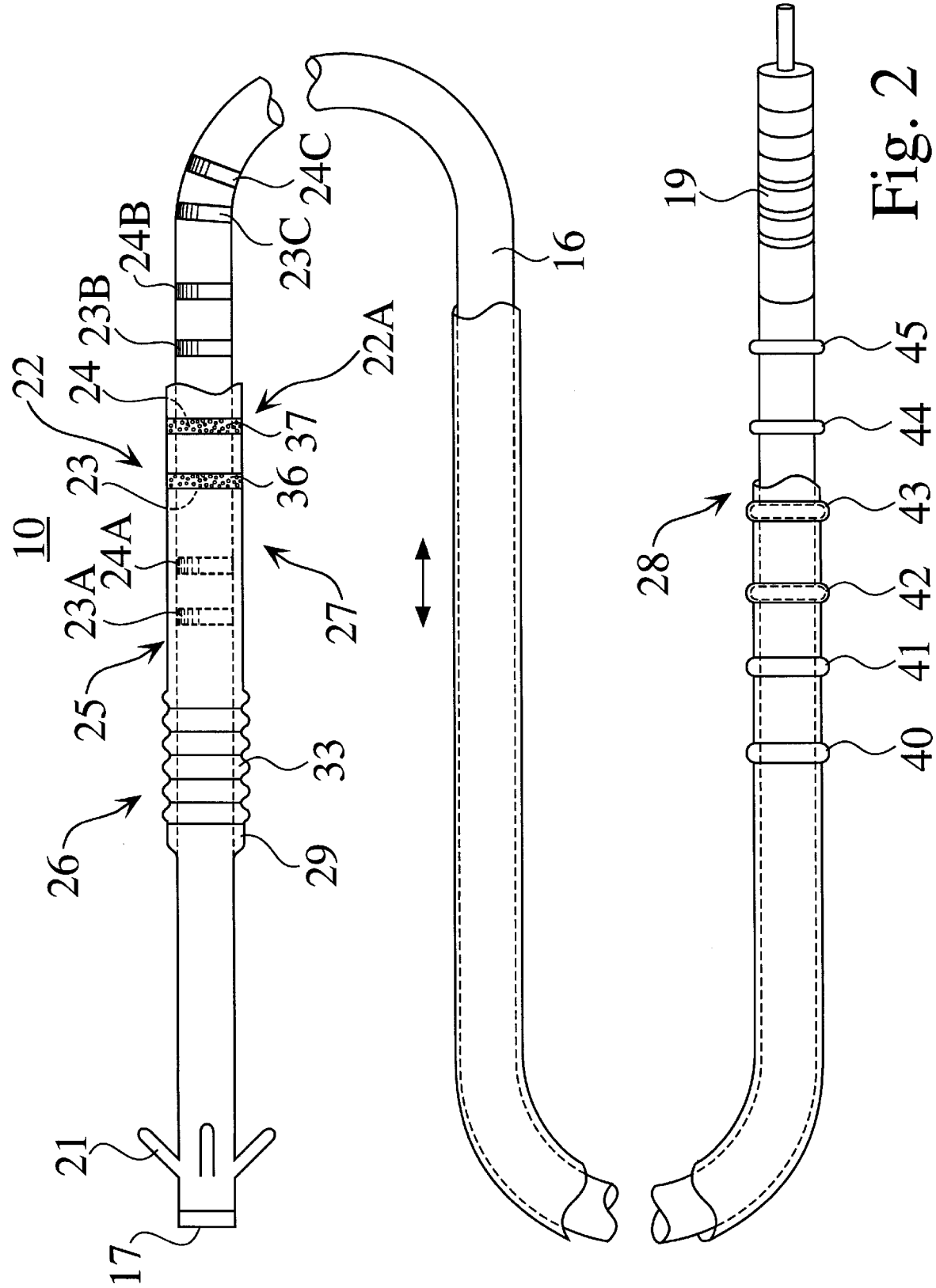
FIG. 2 is an enlarged, partly cutaway view of the lead of FIG. 1 showing an assembly for adjusting the spacing between a pair of effective atrial electrodes and a distal tip.

As illustrated in FIG. 2, the lead 10 further includes an assembly for accurately adjusting the spacing between a pair of effective atrial electrodes 22, 22A and the pacing tip 17 to an optimal position. In the present embodiment, the spacing adjustment assembly is formed of an outer tubular sheath 25 that extends along at least part of the axial length of the lead body 16. For clarity purpose, the outer sheath 25 may be conceptually divided into a distal or ventricular section 26, an atrial section 27, and a proximal section 28.

The outer sheath 25 is generally made of electrically insulating, biocompatible material such as silicone, polyurethane, etc. The distal-most end 29 of the ventricular section 26 is affixed to, or close to the distal end of the lead body 16, to provide a fluid tight seal around the distal end of the outer sheath 25. The distal-most end 29 includes a pliable, expandable member 33. In this particular exemplary embodiment, the expandable member 33 includes an accordion-like bellows which allows the sheath 25 to slide coaxially relative to the lead body 16, so as to permit the selection of an optimal pair of adjacent atrial electrode elements 23, 24, from a plurality of adjacent pairs of atrial electrode elements 23, 24, 23A, 24A, 23B, 24B, 23C, and 24C. It should be understood that the expandable member 33 may be replaced with a different type of mechanism or assembly that allows the flexible, optimal selection of a pair of atrial electrode elements 23, 24. It should also be clear that while the present embodiment is described in relation to the selection of two atrial electrodes 22, 22A, the invention is not limited to this exact number, and a different number of atrial electrodes may alternatively be selected.

The atrial section 27 includes a pair of adjacent windows 36, 37 made of biocompatible porous materials, such as expanded polytetrafluoroethylene (ePTFE). When dry, the windows 36, 37 are not conductive. However, when the windows 36, 37 become wet or hydrated with body fluids, the pores in these windows allow the electrical current to pass through the windows 36, 37. The windows 36, 37 are spaced-apart by a distance that is approximately equal to that of the spacing between two adjacent electrode elements, such as the electrode elements 23, 24. The window 36 in conjunction with the selected electrode element 23 form the atrial electrode 22. Similarity, the window 37 and the electrode element 24 form the atrial electrode 22A. As the expandable member 33 is expanded (or compressed), the windows 36, 37 are slid along the length of the lead body 16, until they overlay, and establish electrical contact with the desired pair of atrial electrode elements, for example 23, 24, thus effectively, forming the atrial electrodes 22, 22A, by electrically exposing the electrode elements 23, 24, while simultaneously causing the remaining atrial electrode elements 23A through 24C to be insulated by the outer tubular sheath 25.

This selectivity feature of the present lead 10 enables the surgeon to adjust the spacing between the windows 36, 37 and the pacing tip 17, before and after the implantation of the lead 10 inside the patient's heart. As a result, a significant amount of guess work for selecting the lead with the appropriate electrode spacing is minimized, in order to achieve optimal sensing and/or pacing through the effective atrial electrode pair 22, 22A floating in the atrium.

The proximal end of the lead 16 may include a plurality of optional visual indicators that provide the surgeon with a clear reference and indication as to which atrial electrode pairs, i.e., 22, 22A have been selected. In this embodiment, the visual indicators are comprised of a plurality of raised portions 40, 41, 42, 43, 44 and 45. In another embodiment the visual indicators may be color coded bars. Once the sheath 25 is properly positioned, and the inter-electrode spacing set, the proximal end of the sheath 25 is secured to the lead body 16 or to the connector 19, by any appropriate method, such as by suturing. While only 8 atrial electrode elements 23 through 24C, and six visual indicators (raised portions 40 through 45) are shown for illustration purpose, it should be clear to a person of ordinary skill in the art that a different number of atrial electrode elements and visual indicators may be selected.

In another exemplary embodiment, each of the atrial electrode elements 23 through 24C has a high surface area, for improved sensing and/or pacing. This high surface area may be achieved for instance, by the proper selection of the material constituting or coating the atrial electrode elements 23 through 24C. For instance, the atrial electrode elements 23 through 24C may be made of any of the following: platinum black, sintered platinum, titanium nitride, platinum roughened surface, MP35N roughened surface, titanium roughened surface, etc.

FIGS. 3 and 4 illustrate the annular structure of the windows 36, 37. While both windows 36, 37 are shown as being identical in size and composition, it should be understood that other lead designs and applications may necessitate variances. In an exemplary embodiment, the inner diameter, the outer diameter, and the width of the windows 36, 37 are 2.8 mm, 3 mm, and 5 mm, respectively. The spacing or distance between the windows 36, 37 may range between approximately 5 mm and 10 mm. Due to the small size of the atrium, it is critical to select the proper spacing between the pacing tip 17 and the atrial electrodes 22, 22A in order to provide optimal atrial sensing. It should be clear that the foregoing dimensions are included herein for illustration purpose, and that other dimensions may alternatively be selected. It should also be understood that each of the windows 36, 37 may be conductive and may be formed of a metallic conductor which is attached to the outer sheath 25, and which is further spring loaded, such that the window is connected to a corresponding atrial electrode element. i.e., 23, via a garter spring.

FIGS. 5 and 6 illustrate the annular structure of the atrial electrode elements 24A, 23, 24, 23B. While the atrial electrode elements 23 through 24B are shown as being identical in size and composition, it should be clear to a person of ordinary skill in the art that these atrial electrode elements 23 through 24B may have different designs. The spacing or distance between two adjacent atrial electrodes 22, 22A may, for instance, range between approximately 5 mm and 10 mm. In the particular embodiment shown in FIG. 5, the atrial electrode elements 24A, 23, 24, 23B are shown to be narrower than the windows 36, 37 to provide an acceptable positioning tolerance, while still maintaining a proper electrical contact between the windows 36, 37 and the selected pair of atrial electrode elements 23, 24. In another embodiment the atrial electrode elements 24A, 23, 24, 23B are wider than the windows 36, 37.

Figure 8:
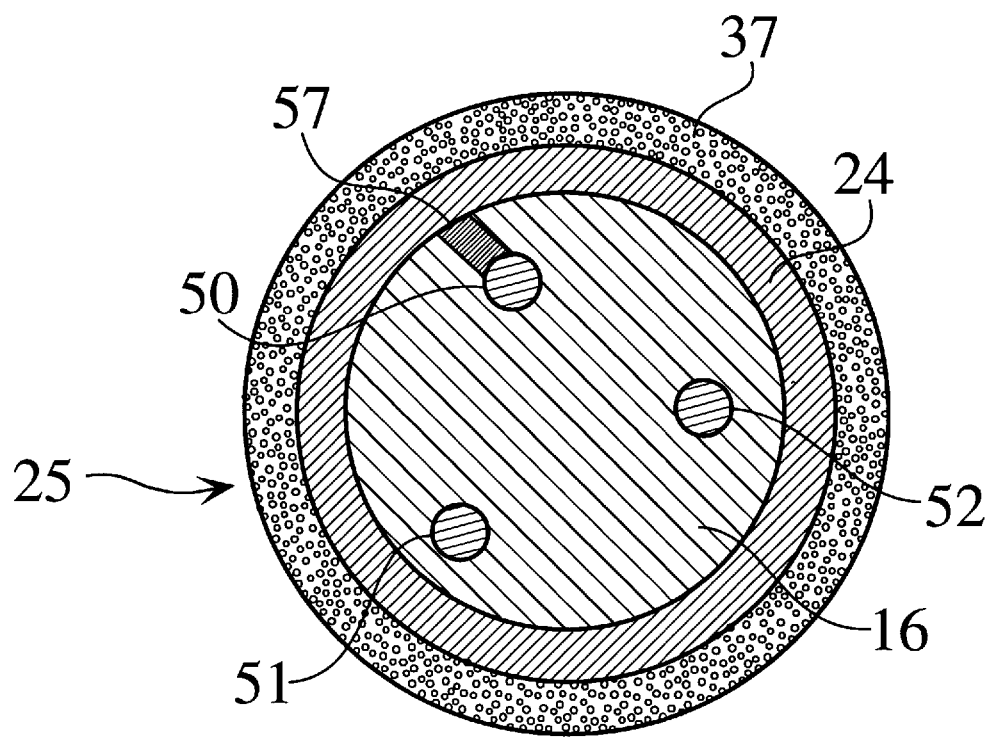

FIGS. 7 and 8 show the sheath 25 snugly assembled over the lead body 16, with the windows 36, 37 in contact and in registration with the atrial electrode elements 23, 24. Three conductors 50, 51, 52 are positioned within the lead body 16. The conductor 52 is connected to the pacing tip 17, while the conductors 50, 51 are connected to the atrial electrode elements 23 through 24C, via a plurality of corresponding conductors such as 56 through 60. In the present embodiment, alternating atrial electrode elements, such as 24, 24A, 24B and 24C, are connected to the conductor 50, while the remaining atrial electrode elements, such as 23, 23A, 23B and 23C are connected to the other conductor 51. It should be noted that while the conductors 50, 51, 52 are shown as straight wires, in the preferred embodiment they may be cables, coiled conductors, coiled cables, or other construction suitable to provide flexibility, strength and fatigue life.

Figure 9:
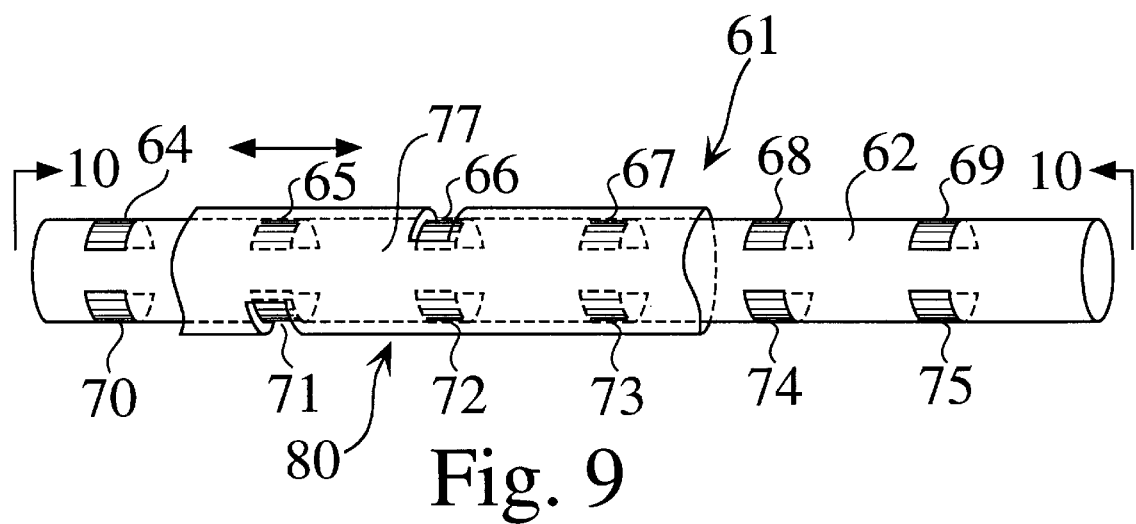
FIGS. 9 and 10 represent a side view and a sectional view, respectively, of part of another transvenous lead made according to the present invention for achieving diagonal bipolar sensing.
Figure 10:
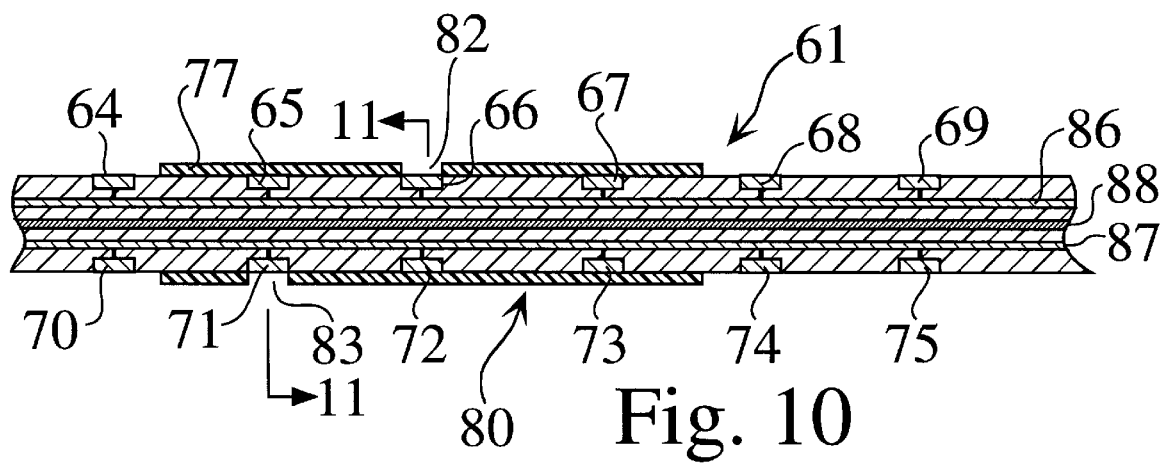
Figure 11:
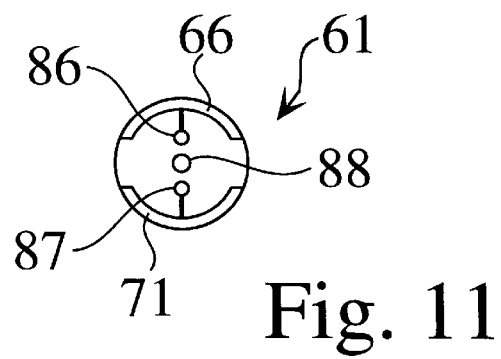
FIG. 11 is a cross-sectional view of the lead of FIGS. 9 and 10, taken along line 11—11 in FIG. 10.

FIGS. 9 through 11 illustrate part of another transvenous pacing lead 61 made according to the present invention. The lead 61 includes a lead body 62 that may be similar or identical to the lead body 16 of the lead 10 of the previous embodiment, whose atrial electrode elements 23 through 24C form complete annular rings (FIG. 6). FIGS. 9 through 11 illustrate a variation to the atrial electrode elements In this alternative embodiment, the lead body 62 includes a plurality of atrial electrode elements 64 through 75.

One distinctive feature of the outer sheath 77 is its window arrangement. For example, the sheath 77 includes a pair of opposing windows 82, 83 that are so dimensioned and positioned on the sheath 77 so as to overlay the selected pair of atrial electrode elements 66, 71, in order to electrically expose these atrial electrode elements and to cause the remaining atrial electrode elements to be shielded or insulated, thus enabling selective and accurate atrial sensing. The spacing between the two windows 82, 83 corresponds to the longitudinal spacing between adjacent atrial electrode elements, i.e., 66, 71. Further details about a single pair diagonal bipolar sensing may be found in U.S. Pat. No. 5,127,403 to Brownlee, which is incorporated herein by reference in its entirety.

The lead 61 further includes a tubular outer sheath 77 which slidably and coaxially engages the lead body 62, in order to enable the surgeon to select the atrial electrodes which provide optimal sensing data. Similarly to the outer sheath 25 of the previous embodiment, the outer sheath 77 may include a distal or ventricular section (not shown), an atrial section 80, and a proximal section (not shown). In one example, the distal section may be similar to the ventricular section 26 of the lead 10. Alternatively, the distal section may be a short tubular extension which is secured to the lead body 62, in a fluid tight manner, after the proper atrial electrode pair has been selected. The proximal section of the lead 61 is similar to the proximal section 28 of the lead 10.

The lead 61 includes three electrical conductors 86, 87, 88 that are positioned within the lead body 62. The conductor 88 extends along the entire axial length of the lead body 62, and is connected to the distal ventricular pacing tip electrode, i.e., 17. The remaining two conductors 86, 87 extend along the length of the proximal and the atrial sections. Each conductor 86, 87 is connected to all the adjacent atrial electrode elements in one part of the lead body 62. In the present embodiment, the conductor 86 is simultaneously connected to the atrial electrode elements 64 through 69, and the conductor 87 is simultaneously connected to the atrial electrode elements 70 through 75. An additional conductor similar to conductor 88 may be used if bipolar sensing/pacing is desired in the ventricle.

In another embodiment, the outer sheath 77 covers approximately the atrial section 80, such that when the proper atrial electrode pair has been selected, then both opposite ends of the outer sheath 77 are secured, in a fluid tight manner to the lead body. In this latter embodiment, all the atrial electrodes, with the exception of the selected atrial electrode pair 66, 71, are shielded by the outer sheath 77.

It should be understood that while the outer sheath 77 has been described herein as comprising two diagonally opposed, hemicyclically shaped windows 82, 83, a different number of windows may optionally be used without departing from the scope of the present invention. It should also be understood that the electrode elements may be alternately longitudinally spaced on opposite sides of the lead and used with annular windows to provide a diagonal electrode arrangement. Also, complete ring electrode elements and half windows may be used to achieve a diagonal electrode arrangement.

It should also be clear that the outer sheath 77 may be secured to the lead body 62 by means of various methods. One such method is to have the outer sheath 77 snugly fit the lead body 62, as described above. Another method would be to select the desired atrial electrodes 66, 71, and to bond the outer sheath 77 to the lead body 62 by means of room temperature vulcanizing medical silicone adhesive. Another method would be to properly position the outer sheath 77 and the lead body 62, and to secure their position by means of sutures. Yet another method would be to use a sheath 77 with an oval cross-section and a lead body 62 with an oval cross-section such that when the outer sheath 77 is properly positioned over the lead body 62 and they are angularly rotated (i.e., 90 degrees), the outer sheath engages the body 62 in a press fit and is locked in position. Other methods may also be used. According to still another method, one or more O-rings (not shown) may be used to seal the outer sheath 77 to the lead body 62.

Figure 12:
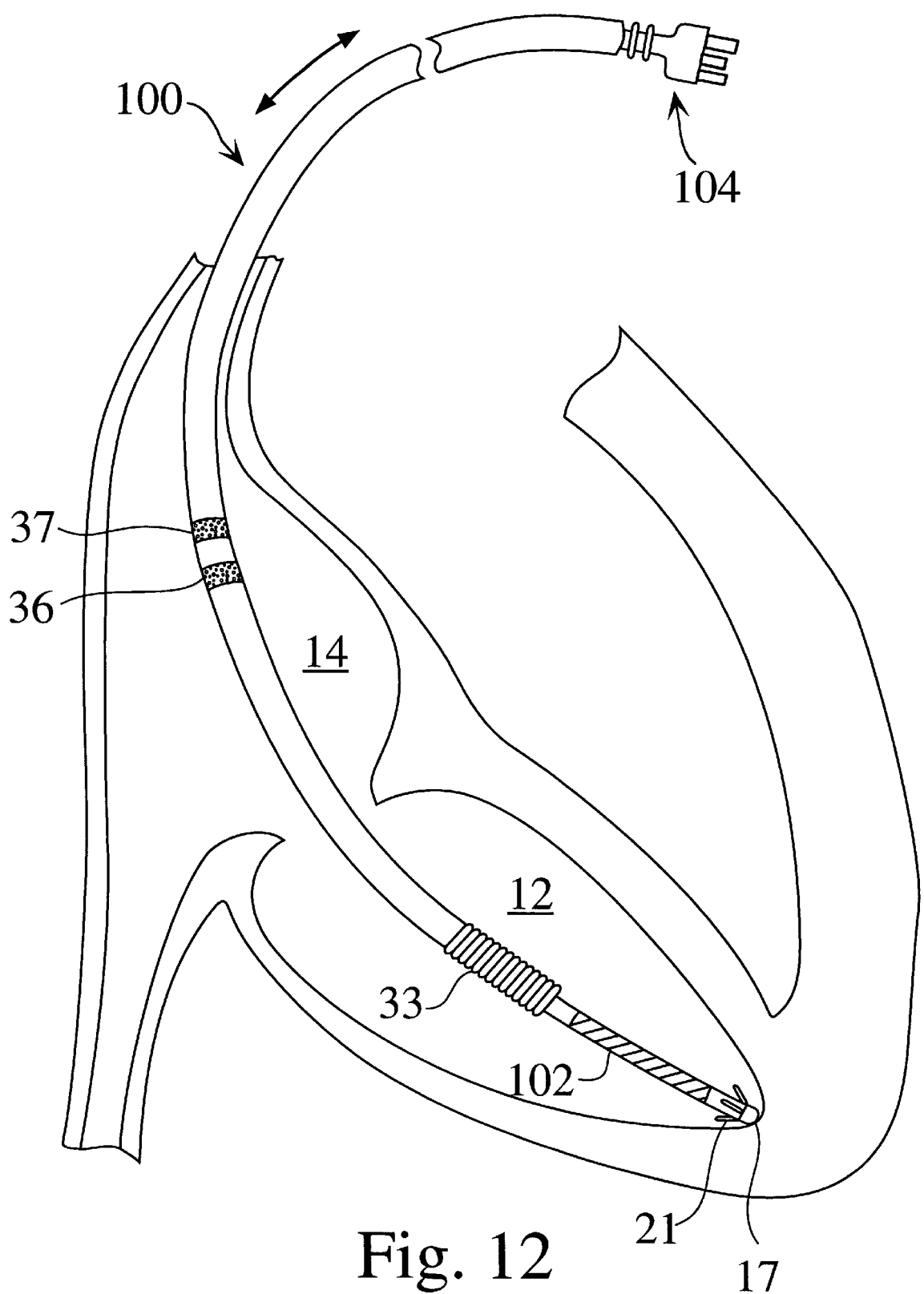
FIG. 12 is a schematic view of another lead embodiment according to the present invention, showing a transvenous implantable defibrillation lead with an RV electrode and a pair of atrial electrodes.
Figure 13:
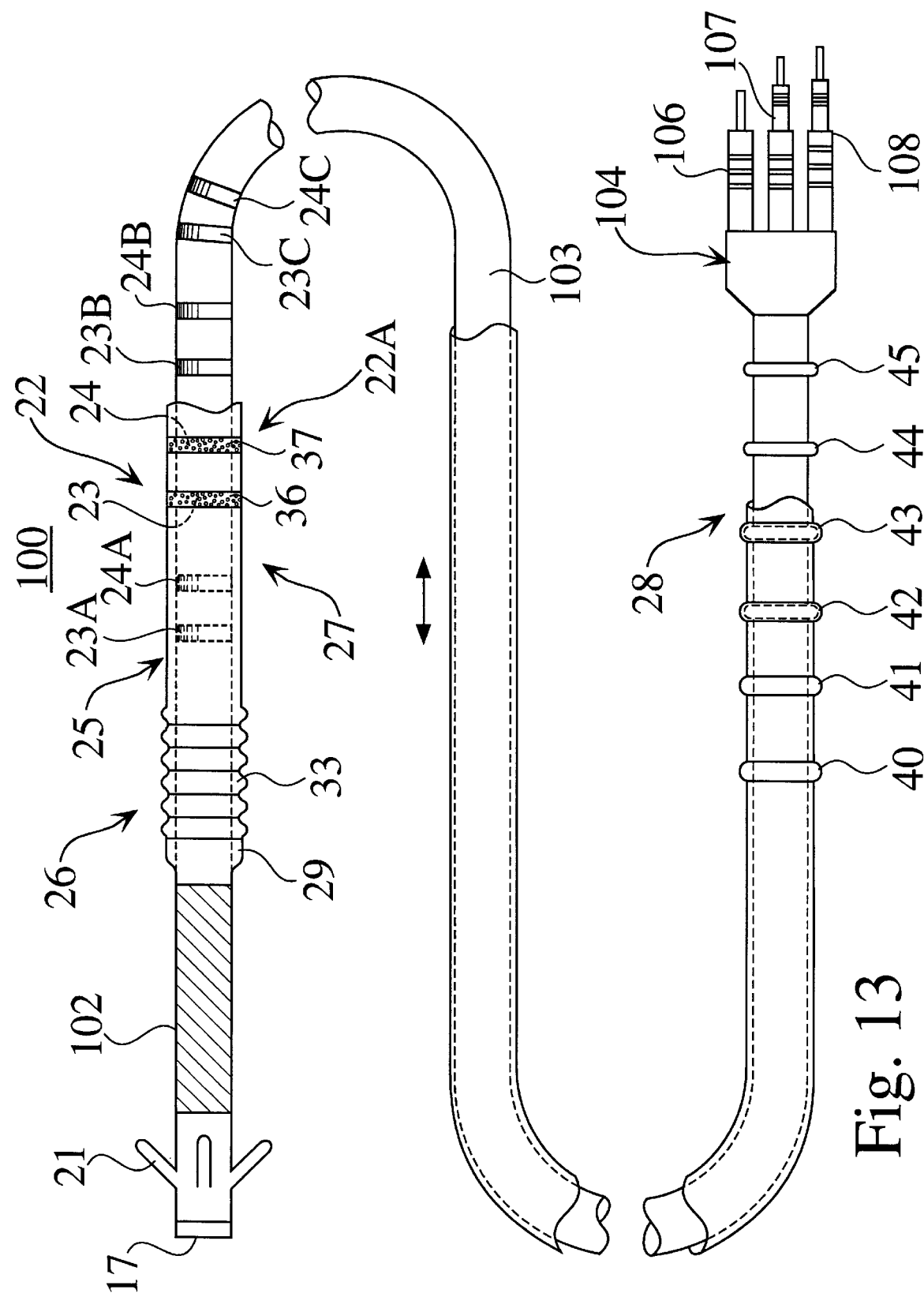
FIG. 13 is an enlarged, partly cutaway view of the lead of FIG. 12, showing an assembly for adjusting the spacing between a pair of atrial electrodes and the distal tip.

FIGS. 12 and 13 illustrate another embodiment of a transvenous implantable defibrillation lead 100 according to the present invention. The lead 100 is generally similar to the lead 10 of the previous embodiment, but further includes a right ventricular defibrillation (RV) electrode 102 for positioning in the right ventricle. Similar reference numerals designate similar components of the two leads 10 and 100. The proximal end of lead 100 includes a connector assembly 104 formed of a plurality of connectors 106, 107, 108, for connection to an implantable cardioverter/defibrillator (ICD), not shown. The ICD is implanted, typically within the patient's abdominal or pectoral region, and includes sensing and detecting circuitry, as well as pulse generating circuitry. When an arrhythmic condition is sensed by the ICD, the ICD delivers cardioverting or defibrillating pulses to the heart through the implanted leads.

The RV electrode 102 may be formed of a wound wire conductive spring electrode, of any construction known in the art. Other electrodes may be alternatively be employed. The distal pacing tip 17 in conjunction with the RV electrode 102 provides bipolar sensing of the heart as well as anti-tachycardia and bradycardia pacing functions. As used herein, antitachycardia pacing is a method of terminating ventricular tachycardia by delivering a series of low energy pulses synchronized with the heart rhythm, and bradycardia pacing is used to increase an abnormally slow heart rate.

In this particular embodiment, the lead 100 includes a lead body 103, on which the RV defibrillation electrode 102 is secured. Other lead configurations are described in U.S. Pat. No. 5,456,706 to Pless et al., entitled A Cardiac Defibrillation Lead Having Defibrillation and Atrial Sensing Electrodes, and commonly assigned to the same assignee of the present application. This patent is incorporated herein by reference in its entirety.

The atrial electrodes 22, 22A are used to sense signals such as waves that initiate in the atrium, to provide information to the defibrillator for discriminating atrial and ventricular rhythms. The atrial electrodes 22, 22A may also be used to pace the atrium. The spacing between the distal pacing tip 17, or the RV defibrillation electrode 102 and the atrial electrodes 22, 22A can be selected as described above in connection with the lead 10.

Figure 14:
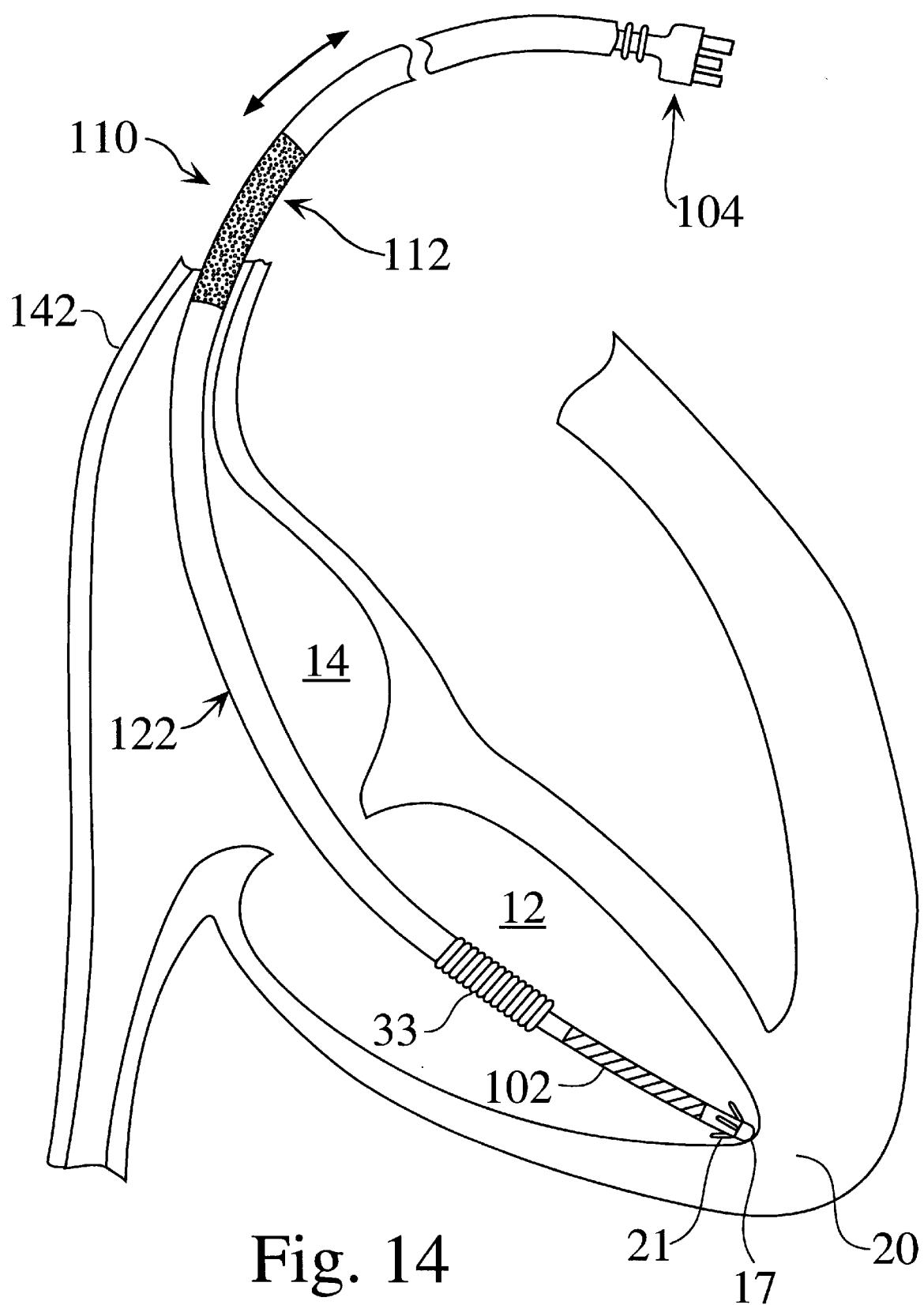
FIG. 14 is a schematic view of another lead embodiment according to the present invention, showing a transvenous implantable defibrillation lead with an RV electrode and an SVC electrode.
Figure 15:
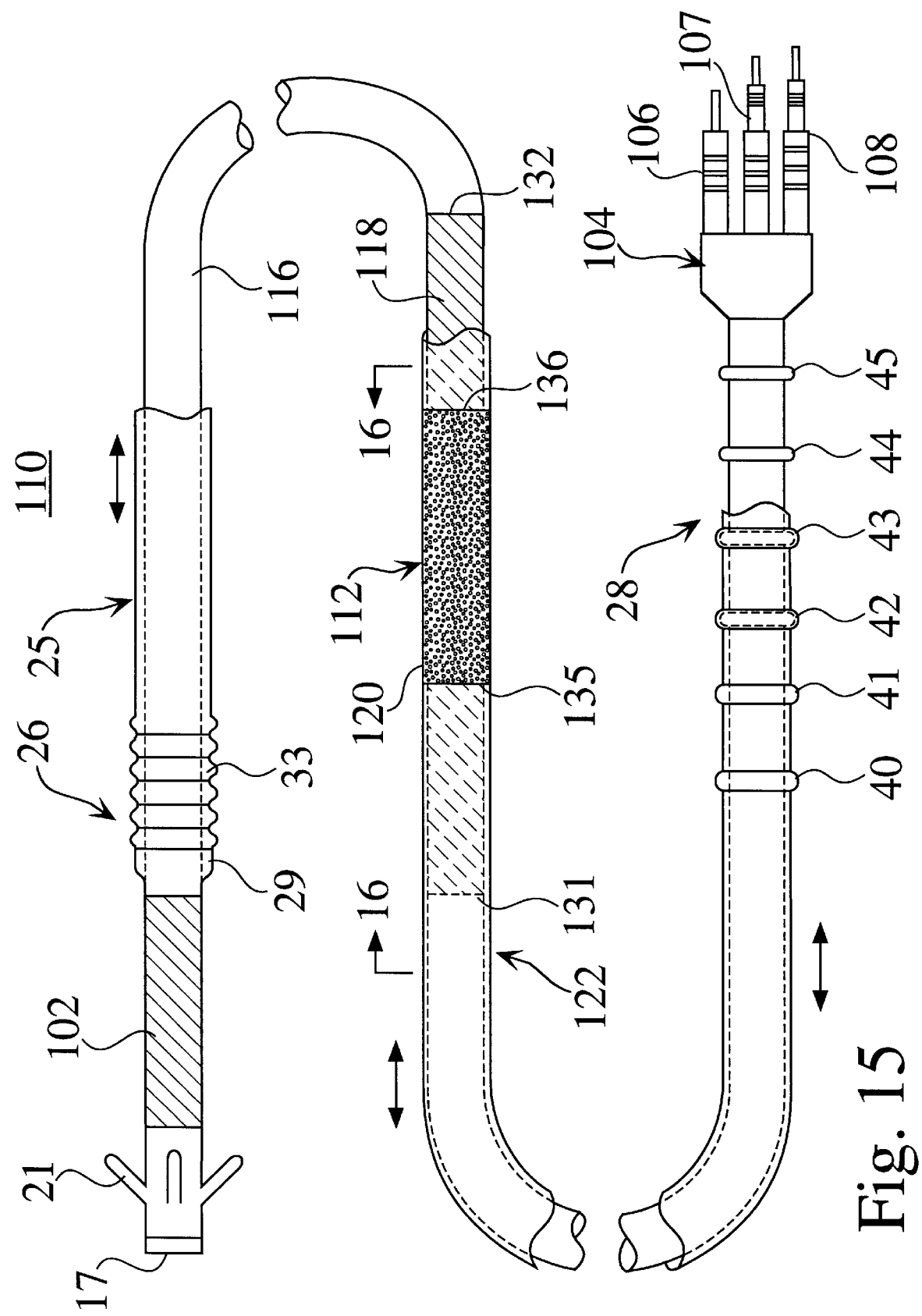
FIG. 15 is an enlarged, partly cutaway view of the lead of FIG. 14, showing an assembly for adjusting the spacing between the RV and SVC defibrillation electrodes.
Figure 16:
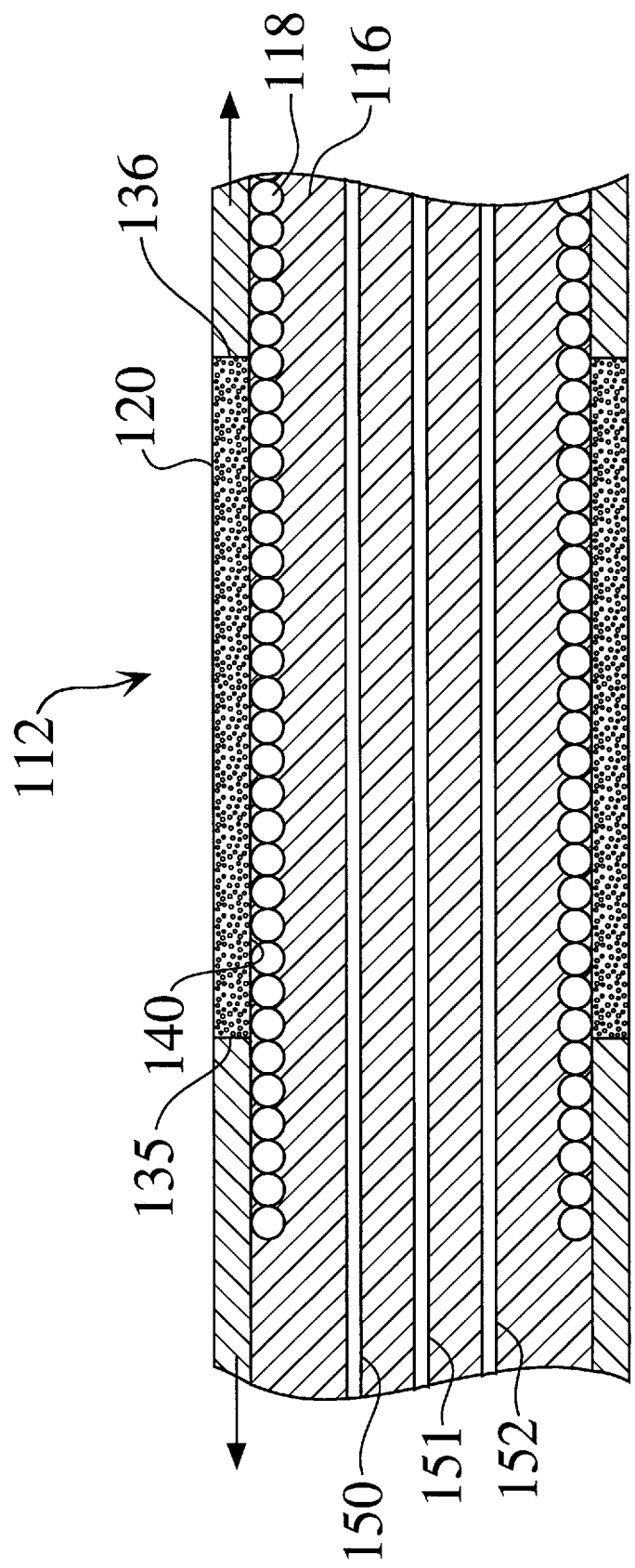
FIG. 16 is an enlarged cross-sectional view of the lead of FIG. 15 taken along line 16—16.

FIGS. 14 through 16 illustrate yet another embodiment of a transvenous implantable defibrillation lead 110 according to the present invention. The lead 110 is generally similar to the lead 100 of the previous embodiment, but further includes a superior vena cava (SVC) electrode 112. Also, the lead 110 differs from the lead 100 in that the lead 110 does not include the atrial sensing electrodes 22, 22A. Similar reference numerals designate similar components of the two leads 100 and 110.

As used herein to describe a location for lead placement, "superior vena cava" and "SVC" may refer to any location near the SVC, such as within the SVC, near or partially within the right atrium 12, or in the innominate vein.

The spacing between the RV electrode 102 and the SVC electrode 112 is essential to optimize the defibrillation field, allowing for a lower defibrillation threshold (DFT). The present lead 110 affords a very flexible and accurate adjustment of the spacing between the two defibrillation electrodes 102, 112. This selectivity of the inter-electrode spacing is achieved by varying the effective position of the SVC electrode 112 along the lead body 116.

The SVC electrode 112 is formed of an SVC coil 118 formed on the lead body 116, and a window 120 that forms part of an outer sheath 122. The outer sheath 122 is axially slidable along the outer periphery of the lead body 116, as explained above in relation to the sheath 25 (FIGS. 1, 2). In general, the sheaths 25 and 122 are similar in function and composition. Each of the two defibrillation electrodes, the RV electrode 102 and the coil 118 of SVC electrode 112 may be of the coiled coil electrode type described in U.S. Pat. No. 5,439,485 to Mar et al., for a "Flexible Defibrillation Electrode of Improved Construction" which is assigned to the assignee of the present application, and which is incorporated herein by reference. However, other electrode types may also be used.

The window 120 is tubular, and is made from a number of smaller windows as described above located close together or entirely from available biocompatible, porous materials, such as expanded polytetrafluoroethylene (ePTFE). The axial length of the window 120 is typically shorter than the axial length of the SVC coil 118, so that when the sheath 122 is slid along the lead body 116, the window 120 also slides between a proximal end 131 and a distal end 132 of the SVC coil 118. In one extreme situation, the expandable member 33 is compressed so that the proximal end 135 of the window 120 is in substantial registration with the distal end 132 of the SVC coil 118, thus effectively insulating almost the entire SVC coil 118. In another extreme situation, the expandable member 33 is expanded so that the distal end 136 of the window 120 is in substantial registration with the proximal end 131 of the SVC coil 118, thus effectively insulating almost the entire SVC coil 118.

In normal use prior to implantation, the surgeon estimates the position of the window 120 over the SVC coil 118, and secures such position by means of available techniques, such as sutures. During implantation, and based on test measurements, the surgeon may decide to adjust the effective position of the SVC electrode 112 by sliding the window 120 along the SVC coil 118, until the inner surface 140 of the window 120 contacts and electrically exposes the optimal portions of the SVC coil 118. Such selective positioning of the window 120 over the SVC coil 118 enables the adjustment of the spacing between the effective SVC electrode 112 (i.e., the window 120) and the RV electrode 102, until optimal defibrillation thresholds are obtained.

The defibrillation lead 110 is inserted transvenously through an incision in a vein such as the cephalic or subclavian vein to a position such that the pacing/sensing tip 17 is positioned against the right ventricular apex 20 of the heart, and the SVC electrode 112 is located near the superior vena cava 142. The position of the SVC electrode 112 is determined in part by its spacing along the lead body 116 from the RV electrode 102. It is not required that the SVC electrode 112 be positioned exactly within the superior vena cava 142, and it may be in the right atrium 14 or the innominate vein. Alternatively, the distal end 132 of the SVC coil 118 may be located within the atrium 14, thus allowing a wide variation of the inter-electrode spacing.

The defibrillation leads described herein, such as the leads 100 and 110, may be used for defibrillation with any combination of the following: a second transvenously placed defibrillation lead, a subcutaneous patch electrode, a subcutaneous array electrode and/or an active pulse generator (i.e., ICD) case. Alternatively, these defibrillation leads could be used with other known electrodes such as epicardial patch electrodes. In yet another embodiment, the defibrillation leads (or catheters) do not include the distal pacing tip 17. In still another embodiment, the distal tip 17 in conjunction with the RV electrode 102 provides sensing of the heart rate as well as pacing functions. This pacing tip 17 may be of any of the numerous constructions known in the art.

As illustrated in FIG. 16, three conductors 150, 151, 152 extend within the lead body 116 for connection to the connectors 106, 107 and 108, respectively. In this respect, the conductor 150 is connected at its distal end to the distal pacing tip 17, the conductor 151 is connected at its distal end to the RV electrode 102, and the conductor 152 is connected at its distal end to the SVC coil 118.

Figure 17:
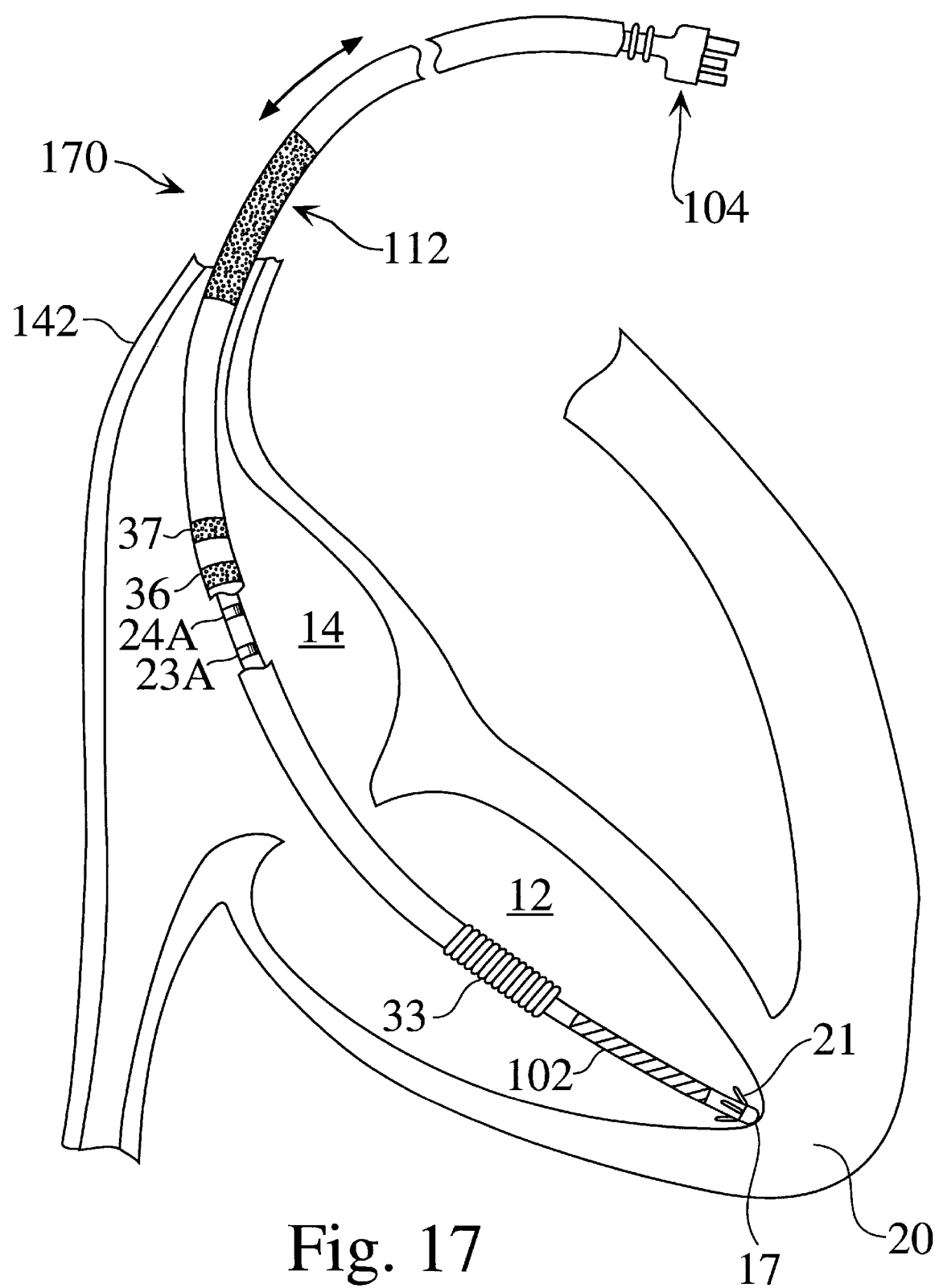
FIG. 17 is a schematic view of another lead embodiment according to the present invention, showing a transvenous implantable defibrillation lead with an RV electrode, an SVC electrode and a pair of adjustable atrial electrodes.
Figure 18:
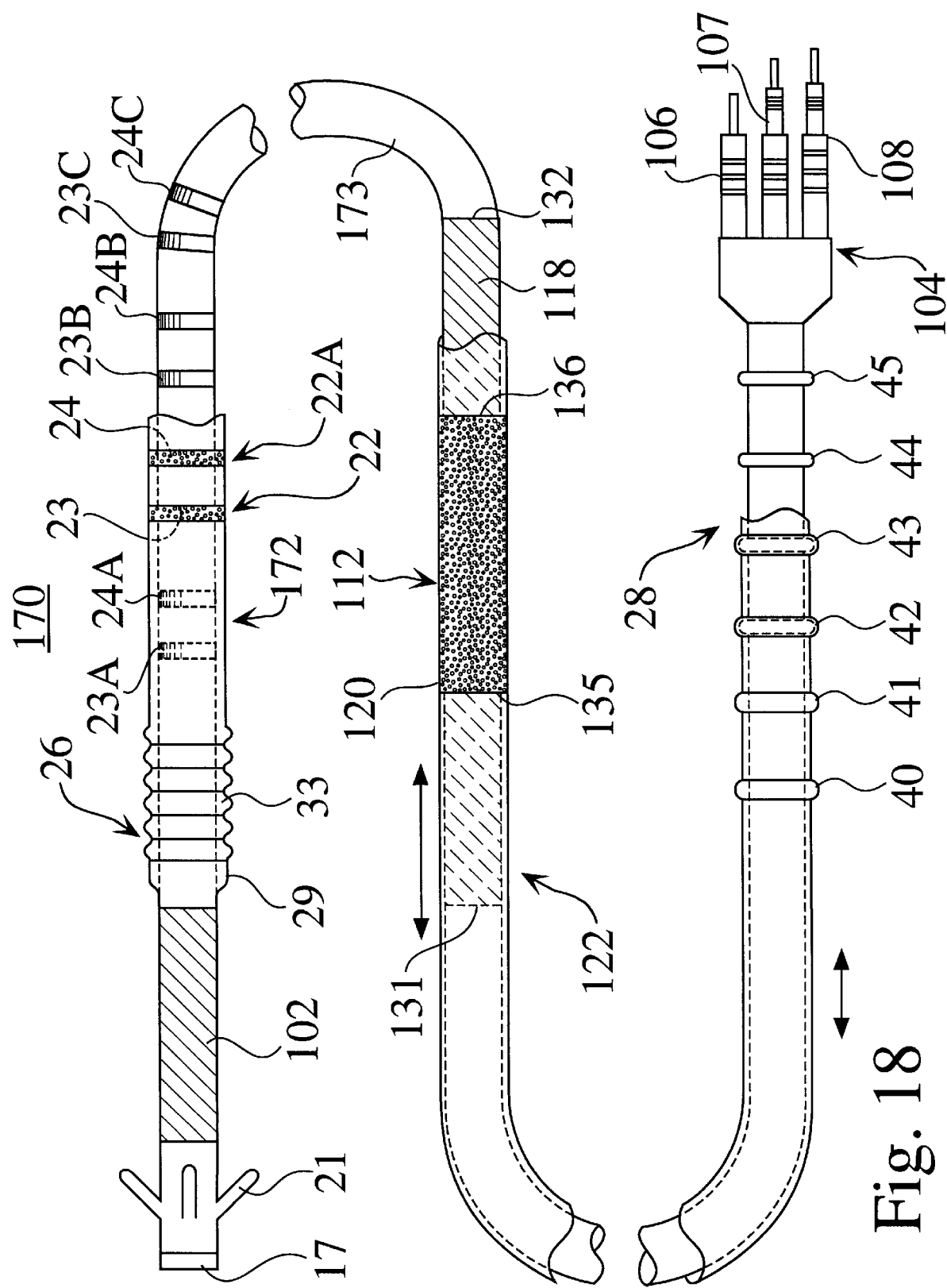
FIG. 18 is an enlarged, partly cutaway view of the lead of FIG. 17, showing an assembly for adjusting the spacing between a pair of atrial sensing electrodes and the pacing tip, and the spacing between the RV and SVC defibrillation electrodes.

FIGS. 17, 18 illustrate still another embodiment of a transvenous implantable defibrillation lead 170 according to the present invention. The lead 170 is generally similar to the lead 100 (FIG. 13) and the lead 110 (FIG. 15) of the previous embodiments, but may be viewed as a combination of both these leads 100 and 110, with similar reference numerals designating similar components.

The lead 170 includes two atrial sensing electrodes 22, 22A adjustably positioned between the RV electrode 102 and the SVC electrode 112, at a distance from the pacing tip 17 (or another fixed reference point), to provide optimal positioning within the atrium in order to ensure adequate bipolar sensing and pacing. The lead 170 further includes a slidable outer sheath 172 and a lead body 173. The outer sheath 172 is formed of the expandable member 33 at its distal end, the windows 36, 37 and the window 120. The lead body 173 supports the RV defibrillation electrode 102, the atrial electrode elements 23 through 24C, the SVC coil 118, and the raised portions 40, 41, 42, 43, 44 and 45. The lead body 173 is attached to the connector assembly 104.

In this particular embodiment, the spacing between the window 120 and the windows 36, 37 is fixed. As a result, as the expandable member 33 is expanded (or compressed), the outer sheath 172 slides along the lead body 173, such that the windows 36, 37 are moved until they overlay the desired pair of atrial electrode elements, for instance 23, 24, thus effectively forming the atrial electrodes 22, 22A, by electrically exposing the atrial electrode elements 23, 24, while simultaneously causing the remaining atrial electrode elements 23A through 24C to be insulated. Thus, in this example, atrial sensing is accorded a primordial role, while the positioning of the SVC electrode 112 is secondary, and the spacing between the atrial electrodes 22, 22A and the distal pacing tip 17 is determinative. In another example, the outer sheath 172 is slid along the lead body 173 until the desired effective and optimal SVC electrode 112 is reached, without compromising the atrial pacing and sensing function. In this embodiment the spacing between the defibrillation electrodes 102 and 112 is determinative.

Figure 19:
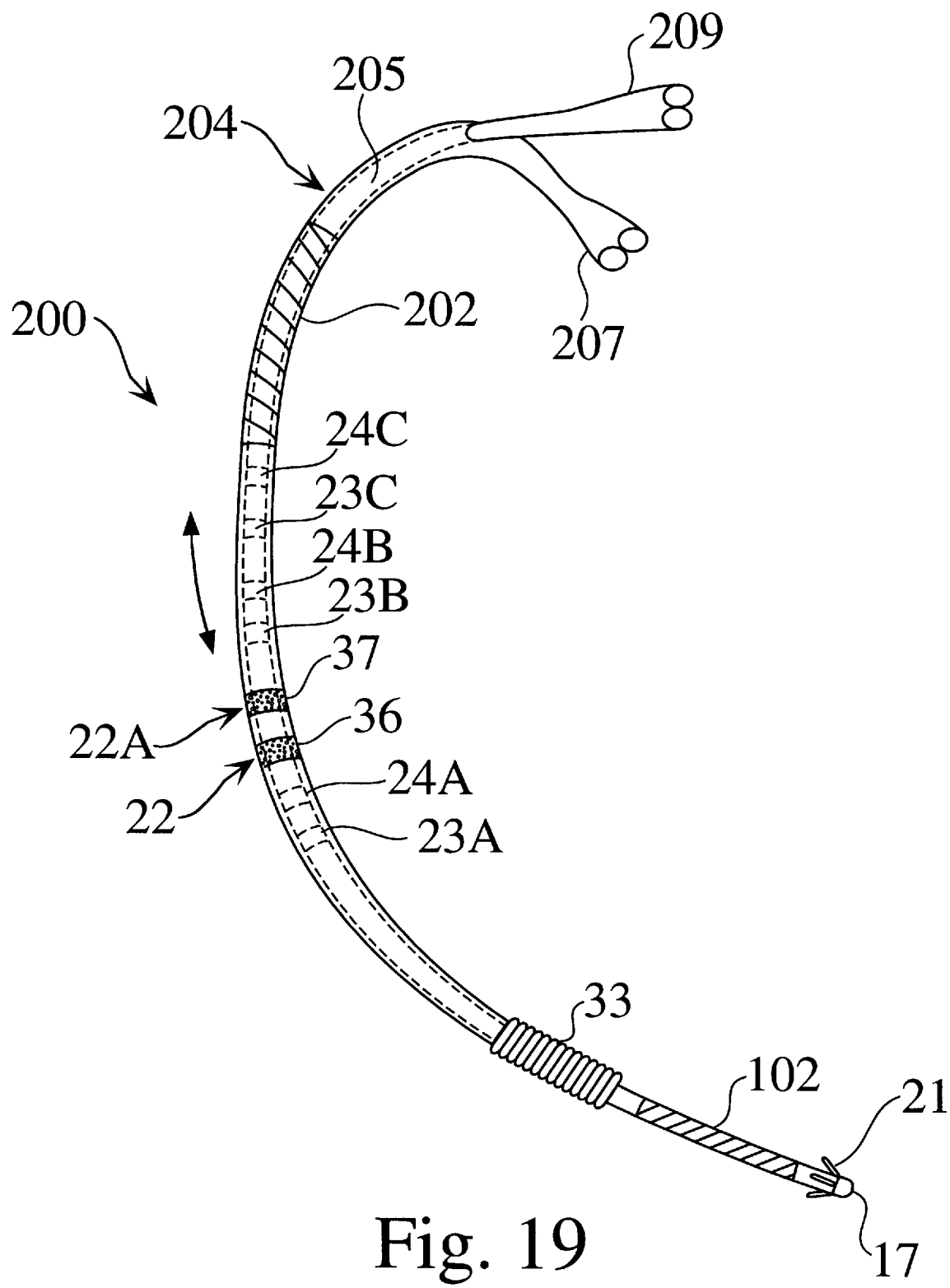
FIG. 19 illustrates a further embodiment of a transvenous implantable defibrillation lead according to the present invention.

FIG. 19 illustrates a further embodiment of a transvenous implantable defibrillation lead 200 according to the present invention. The lead 200 is generally similar to the lead 170 (FIG. 17), with similar reference numerals designating similar components. The lead 200 includes two atrial sensing electrodes 22, 22A that are optimally positioned between the RV electrode 102 and an SVC electrode 202, to ensure adequate bipolar sensing. The lead 200 further includes a slidable outer sheath 204 and a lead body 205 (shown mostly in dashed lines). The outer sheath 204 includes the expandable member 33 at its distal end, and the windows 36, 37. The outer sheath 204 supports the SVC electrode 202 which may be formed of a coiled conductor as is known in the art.

The outer sheath 204 terminates in a connector 207, and accommodates electrical conductors (not shown) that connect the SVC electrode 202 to the connector 207. The lead body 205 extends within the outer sheath 204, and supports the RV defibrillation electrode 102, the atrial electrode elements 23 through 24C. It is attached to a connector 209, and accommodates electrical conductors (not shown) that connect the distal pacing tip 17, the atrial electrode elements 23 through 24C, and the RV electrode 102 to the connector 209.

In this particular embodiment, the spacing between the SVC electrode 202 and the windows 36, 37 is fixed. As a result, when the expandable member 33 is expanded (or compressed), the outer sheath 204 slides along the lead body 205, such that the windows 36, 37 are moved until they overlay the desired pair of atrial electrode elements, for instance 23, 24, thus effectively forming the atrial electrodes 22, 22A, by electrically exposing the electrode elements 23, 24, while simultaneously insulating the remaining atrial electrode elements 23A through 24C. Thus, in this example, the spacing between the atrial electrodes 22, 22A and the distal pacing tip 17 is determinative and has primary consideration. In another example, the outer sheath 204 is slid along the lead body 205 until the desired and optimal spacing between the SVC electrode 202 and the RV electrode 102 is reached without compromising the atrial sensing and pacing function. In a variation to this embodiment, the atrial electrodes 22 and 22A are replaced by two atrial ring electrodes that are positioned on the outer sheath 204, and that are slidably relocatable relative to the pacing tip 17, as the expandable member 33 is either compressed or expanded.

Figure 20:
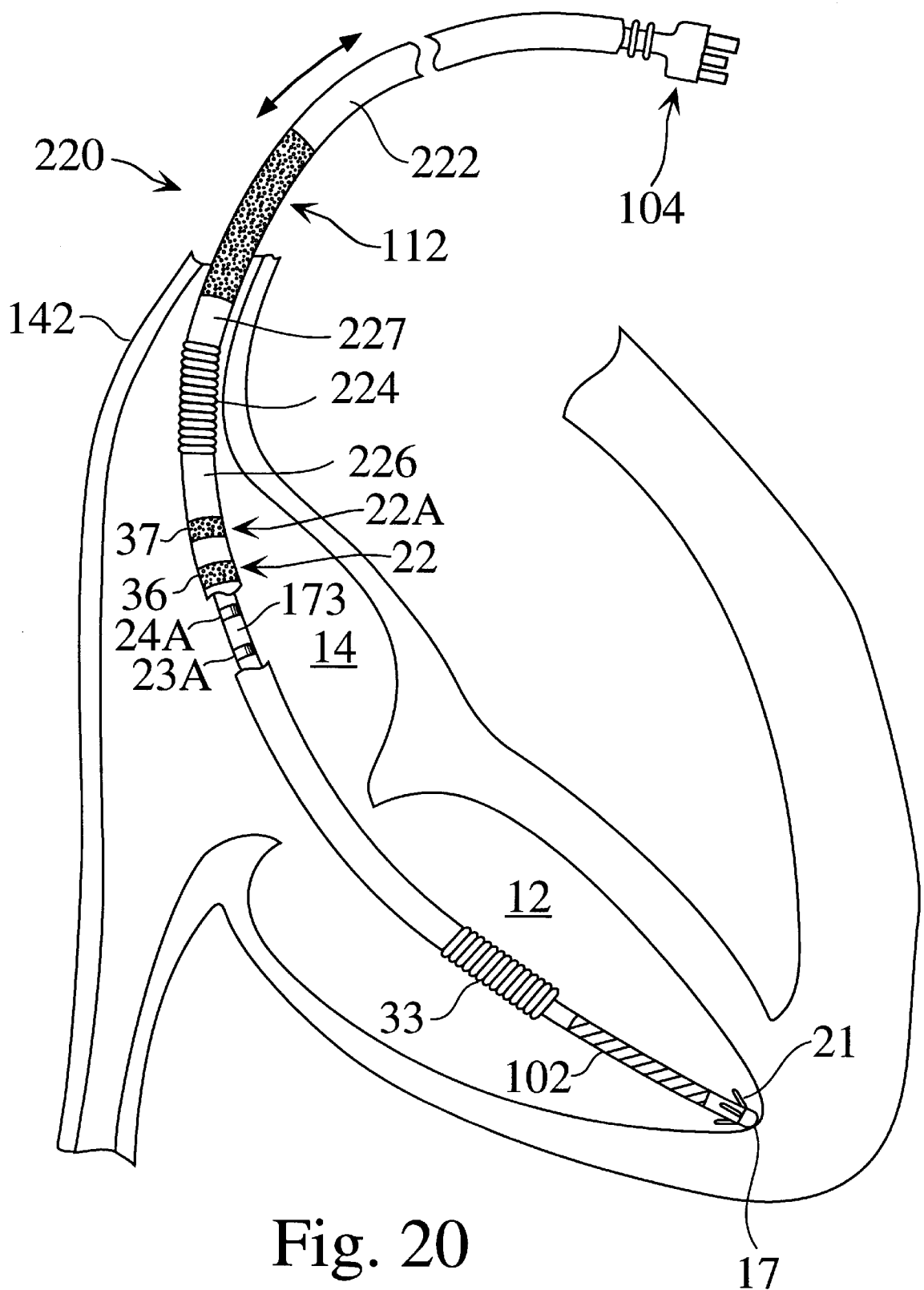
FIG. 20 is a schematic view of still another lead embodiment according to the present invention, showing a transvenous implantable defibrillation lead with an RV electrode, an SVC electrode, a pair of adjustable atrial electrodes and two spacing adjustment mechanisms.

FIG. 20 illustrates another embodiment of a transvenous implantable defibrillation lead 220 according to the present invention. The lead 220 is generally similar in design and function to the lead 170 (FIG. 17), with similar reference numerals designating similar components. The lead 220 differs from the lead 170 in one or both of the following aspects.

The first distinction between these two leads 170, 220 is that the lead 220 includes an outer sheath 222 having one or more additional adjustable or expandable members 224 positioned along its axial length. In this example, the adjustable member 224 is positioned between the window 37 and the SVC electrode 112 defined by window 120 (not shown). The adjustable member 224 is connected between two rigid sections 226, 227 of the outer sheath 222, and permits the adjustment of the spacing of the SVC electrode 112 relative to a fixed reference point on the lead body. The adjustable member 33 allows the spacing between the distal pacing tip 17 and the effective atrial sensing electrode pair 22, 22A to be independently adjusted. The adjustable members 33 and 224 provide fluid tight envelopes that prevent the body fluid from leaking between the outer sheath 222 and the lead body 173.

The second distinction between these two leads 170, 220 is that the outer sheath 222 of the lead 220 may optionally include more than one pair of windows. This feature permits the lead 220 to select one or more pair of effective atrial sensing electrodes, i.e., 23, 24, by simply positioning the windows 36, 37 over, and in contact with the underlying atrial electrode elements 23 through 24C.

Figure 21:
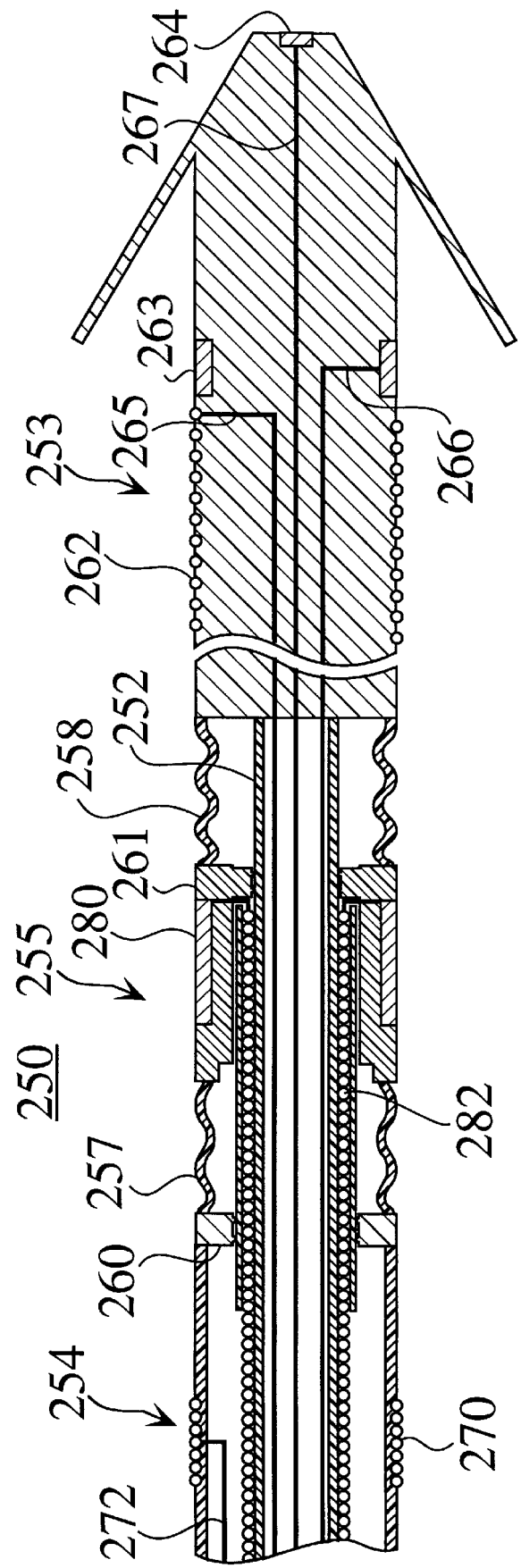
FIG. 21 represents an enlarged, cross-sectional view of another lead made according to the present invention.

FIG. 21 represents an enlarged cross-sectional view of a lead 250, which generally includes an inner slidable lead body 252 and three assemblies that are selectively positionable relative to one another. These three assemblies are: a distal RV electrode assembly 253, a proximal SVC defibrillation electrode assembly 254, and an intermediate atrial sensing/pacing assembly 255. These three assemblies 253, 254, 255 are adjustably connected by means of flexible bellows-like members 257, 258.

The flexible members 257, 258 enable the lead 250 to maintain a substantially uniform outer diameter along its axial length, for simplifying lead explantation, and for reducing the growth of fibrotic tissue on the lead 250. They also provide added tensile structural strength, thus providing further advantages during explantation. The flexible members 257, 258 are made of robust, flexible, biocompatible material, such as ePTFE, and prevent tissue in-growth within the lead 250. They may also be coated with a layer of silicone, or, alternatively, they may be impregnated with silicone, or a similar material, such as polyurethane, in order to provide a fluid seal.

The lead 250 further includes an O-ring seal 260 between the proximal SVC defibrillation electrode assembly 254, and the intermediate sensing/pacing assembly 255, and another O-ring seal 261 between the distal RV electrode assembly 253, and the intermediate sensing/pacing assembly 255. These O-ring seals 260, 261 may be added whenever the flexible members 257, 258 are not made of a material capable of providing a fluid seal to the interior of the lead 250, such as ePTFE.

The three assemblies 253, 254, 255 will now be described in more detail. The distal RV electrode assembly 253 includes an RV electrode 262, an optional RV sense ring 263, and the pacing tip 264. A conductor 265 is connected to the RV electrode 262, a conductor 266 is connected to the RV sense ring 263, and another conductor 267 is connected to the pacing tip 264. These three conductors 265, 266, 267 travel along the full length of the lead 250 for connection to a connector or connectors (not shown). All the elements of the distal RV electrode assembly 253 are fixed relative to each other.

The proximal SVC defibrillation electrode assembly 254 generally includes an SVC defibrillation electrode 270 which is electrically connected to a conductor 272. The conductor 272 is connected to a connector (not shown) at the proximal end of the lead 250. All the elements of the proximal SVC defibrillation electrode assembly 254 are fixed relative to each other. However, the proximal SVC defibrillation electrode assembly 254 is adjustably positionable relative to the distal RV electrode assembly 253 and the intermediate atrial sensing/pacing assembly 255, by means of the flexible members 257, 258.

The intermediate atrial sensing/pacing assembly 255 includes one or more atrial electrodes 280, as described herein. The atrial electrodes 280 are electrically connected to a conductor 282. A number of such atrial electrodes 280 could be positioned on the atrial sensing/pacing assembly 255, as shown in the embodiments described herein. All the elements of the intermediate atrial sensing/pacing assembly 255 are fixed relative to each other. However, the intermediate atrial sensing/pacing assembly 255 is adjustably positionable relative to the proximal SVC defibrillation electrode assembly 254 and the distal RV electrode assembly 253, by means of the flexible members 257, 258.

The foregoing description of the inventive embodiments has been presented for purposes of illustration and description. It is not intended to be exhaustive or to limit the invention to the precise forms described. Various modifications of the system components and methods of operation may be employed in practicing the invention. It is intended that the following claims define the scope of the invention, and that the structures and methods within the scope of these claims and their equivalents be covered thereby.

What is claimed is:

1. A lead with inter-electrode spacing adjustability, to be introduced in a patient's body, comprising in combination:
    an elongated lead body extending between a tip at a distal end, and a proximal end;
    an outer sheath extending coaxially with at least part of said lead body, between said proximal end and said distal end, said outer sheath including a ventricular section in proximity to said distal end of said lead body having an expandable member for enabling said outer sheath to slide coaxially relative to said lead body, a proximal section substantially overlaying said proximal end of said lead body, and an atrial section that is slidably adjustable between said ventricular section and said proximal section; and
    one or more effective electrodes including one or more windows that are positioned along said outer sheath, adjustable relative to said tip by sliding said outer sheath along said lead body.

2. The lead according to claim 1, wherein a distal end of said ventricular section of said outer sheath is secured to said distal end of said lead body, to provide a fluid tight seal.

3. The lead according to claim 1, wherein said lead body includes a plurality of adjacent electrode elements; and
    wherein said atrial section of said outer sheath includes at least one window which is adjustably positionable over at least one of said plurality of electrode elements, to form an effective electrode.

4. The lead according to claim 3, wherein said atrial section includes two adjacent windows that are positionable over two adjacent electrode elements, to form two effective atrial electrodes.

5. The lead according to claim 4, wherein said two windows are made of biocompatible, porous material.

6. The lead according to claim 5, wherein said electrode elements are annularly shaped ring electrodes.

7. The lead according to claim 6, wherein said two effective atrial electrodes are used for atrial sensing.

8. The lead according to claim 3, further including a connector at said proximal end of said lead body, for connection to a pulse generator.

9. The lead according to claim 4, wherein said proximal end of said outer sheath includes a plurality of visual indicators to provide a record of a selected position of said electrode elements.

10. The lead according to claim 5, wherein said ventricular and proximal sections of said outer sheath are substantially made of electrically insulating biocompatible material.

11. The lead according to claim 6, wherein said two effective atrial electrodes are used for atrial pacing.

12. A lead with inter-electrode spacing adjustability, to be introduced in a patient's body, comprising in combination:
    an elongated lead body extending between a tip at a distal end, and a proximal end;
    an outer sheath extending coaxially with at least part of said lead body, between said proximal end and said distal end;
    a superior vena cava (SVC) defibrillation electrode formed on said outer sheath for positioning in the area of a patient's superior vena cava; and
    one or more effective electrodes including one or more windows that are positioned along said outer sheath, adjustable relative to said tip by sliding said outer sheath along said lead body.

13. The lead according to claim 12, and further including a right ventricular defibrillation (RV) electrode positioned along said distal end of said lead body.

14. A lead with inter-electrode spacing adjustability, to be introduced in a patient's body, comprising in combination:
    an elongated lead body extending between a tip at a distal end, and a proximal end;
    an outer sheath extending coaxially with at least part of said lead body, between said proximal end and said distal end including a first expandable member formed on said outer sheath for enabling said outer sheath to slide coaxially relative to said lead body; and
    one or more effective electrodes including one or more windows that are positioned along said outer sheath, adjustable relative to said tip by sliding said outer sheath along said lead body.

15. The lead according to claim 14, and further including a defibrillation electrode formed on said outer sheath.

16. The lead according to claim 14, and further including a right ventricular defibrillation (RV) electrode positioned along said distal end of said lead body.

17. The lead according to claim 14, and further including a superior vena cava (SVC) defibrillation electrode comprised of an SVC conductor formed on said lead body, and a window forming part of said outer sheath and slidably covering and exposing at least part of said SVC conductor, so as to define an effective SVC defibrillation electrode therewith.

18. The lead according to claim 14, wherein said first expandable member is formed on a distal section of said outer sheath and further including a second expandable member formed on a proximal section of said outer sheath.

19. A lead with inter-electrode spacing adjustability, to be introduced in a patient's body, comprising in combination:
    a distal RV electrode assembly;
    a proximal SVC defibrillation electrode assembly;
    an intermediate atrial sensing/pacing assembly; and a first flexible member for adjustably interconnecting said distal RV electrode assembly and said intermediate atrial sensing/pacing assembly and a second flexible member for adjustably interconnecting said proximal SVC defibrillation electrode assembly and said intermediate atrial sensing/pacing assembly.

20. A lead with inter-electrode spacing adjustability, to be introduced in a patient's body, comprising in combination:

an elongated lead body extending between a tip at a distal end, and a proximal end;

an outer sheath extending coaxially with at least part of said lead body, between said proximal end and said distal end;

an electrode positioned at least in part on said outer sheath; and one or more flexible members connecting said outer sheath and said lead body, for causing said electrode to be positioned adjustably relative to said tip.

21. The lead according to claim 20, wherein said electrode includes a defibrillation electrode comprised of a defibrillation conductor formed on said lead body, and a window which forms part of said outer sheath and which slidably covers and exposes at least part of said defibrillation conductor.

22. A lead with inter-electrode spacing adjustability, to be introduced in a patient's body, comprising in combination:

an elongated lead body extending between a tip at a distal end, and a proximal end;

an outer sheath extending coaxially with at least part of said lead body, between said proximal end and said distal end;

said lead body including a plurality of generally hemicyclically shaped atrial electrode elements disposed in diagonally opposing pairs; and said outer sheath including a pair of opposing windows that are shaped and positioned on said outer sheath so as to overlay a selected pair of said plurality of atrial electrode elements, in order to electrically expose said selected pair.

* * * * *